United States Patent
Socci et al.

(10) Patent No.: US 6,740,314 B2
(45) Date of Patent: May 25, 2004

(54) NAIL ENAMEL COMPOSITIONS CONTAINING BISMUTH OXYCHLORIDE

(75) Inventors: Robert L. Socci, Cedar Grove, NJ (US); Anatoly Ismailer, Roslyn Heights, NY (US)

(73) Assignee: Kirker-Enterprises, Inc., Paterson, NJ (US)

( * ) Notice: Subject to any disclaimer, the term of this patent is extended or adjusted under 35 U.S.C. 154(b) by 0 days.

(21) Appl. No.: 10/156,875

(22) Filed: May 29, 2002

(65) Prior Publication Data

US 2003/0012750 A1 Jan. 16, 2003

Related U.S. Application Data

(63) Continuation-in-part of application No. 09/611,900, filed on Jul. 7, 2000, now Pat. No. 6,565,835.

(51) Int. Cl.$^7$ ............................. A61K 7/00; A61K 7/04
(52) U.S. Cl. .......................................... 424/61; 424/401
(58) Field of Search .................................... 424/61, 401

(56) References Cited

U.S. PATENT DOCUMENTS

| | | | |
|---|---|---|---|
| 3,438,796 | A | 4/1969 | Hanke |
| 4,116,628 | A | 9/1978 | Hesse et al. |
| 4,192,691 | A | 3/1980 | Armanini |
| 5,093,108 | A | 3/1992 | Pappas et al. |
| 5,346,692 | A | 9/1994 | Wohlrab et al. |
| 5,688,494 | A * | 11/1997 | Graves et al. ................ 424/61 |
| 5,977,217 | A | 11/1999 | Socci et al. |
| 5,993,837 | A | 11/1999 | Calello et al. |
| 6,139,822 | A | 10/2000 | Socci et al. |
| 6,156,325 | A * | 12/2000 | Farer et al. .................. 424/401 |

OTHER PUBLICATIONS

Material Safety Data Sheet and Sales Specification, MD–BOTH Industries, pp. 1–4.
Product Data Sheet for Starbrite 1100 EAX Aluminum Dispersion, Silberline Manufacturing Co., Inc.
Technical Data Sheet PMU 20–05, BYK–410, BYK–Chemie USA, pp. 1–2.
Technical Sheet of Technical Properties of CAB–381–0.5 BP, CAB–381–2 BP and CAB–381–20 BP.
Dianal—Acrylic Bead Resins Commercial Products Summary Chart—Dianal America, Inc.
Tech Data Sheet on Metalure, Obron Atlantic Corp., pp. 1–3.
BYK Gardner Technical Sheet on Haze–Gloss.
Chapter 41 on Gloss, pp. 470–479, by Hammond and Kigle–Boeckler.
Technical Data Sheet on Typical Properties of CAB, CAP and CA.
Eckert–Werke Article entitled "Metallic Gloss of Impressive Brillance", pp. 1–3.
Information Sheet IPEX 2002 on Eckert–Werke.
Information Sheet from Eckert–Werke on Metalure.
Eckert–Werke Article entitled "Adding a Shine to the World", pp. 1–2.

* cited by examiner

Primary Examiner—James M. Spear
Assistant Examiner—Sharon Howard
(74) Attorney, Agent, or Firm—Lerner, David, Littenberg, Krumholz & Mentlik, LLP

(57) ABSTRACT

Nail enamel compositions of the present invention for coating natural or synthetic human nails broadly include the ingredients of one or more film forming components, preferably nitrocellulose having a molecular weight greater than 56,000, one or more solvents and bismuth oxychloride.

25 Claims, No Drawings

NAIL ENAMEL COMPOSITIONS CONTAINING BISMUTH OXYCHLORIDE

CROSS REFERENCE TO RELATED APPLICATIONS

The present application is a continuation-in-part of copending U.S. patent application Ser. No. 09/611,900, filed Jul. 7, 2000, now U.S. Pat. No. 6,565,835 entitled "Nail Enamel Compositions Containing Aluminum Platelets", the disclosure of which is hereby incorporated by reference herein.

BACKGROUND OF THE INVENTION

The present invention relates in general to nail enamel compositions, and more particularly, to nail enamel compositions containing bismuth oxychloride for forming a film having a glossy appearance over natural or synthetic human nails.

Nail enamel compositions include a class of nail care products regularly used by women as part of their beauty care routine. These nail care products are available in a multitude of product formulations, from clears to a variety of colors. Typically, clear nail enamel compositions include a film forming polymer, a film forming resin, a plasticizer and one or more solvents. In the case of a color nail enamel composition, the product may also include a thixotropic compound, a suspending agent and one or more pigments, or in the alternative, an organic coloring polymer may be used. In addition to these components, a number of optional and proprietary components are often included such as UV light absorbers, moisturizers, stabilizers, fragrances and the like.

Nail enamel compositions have heretofore been formulated in an infinite number of colors. Often, the manufacturers would produce nail enamel compositions having the same popular colors as their competitors. This provided little distinction between nail enamel products of different manufacturers to the ultimate consumer. Nail enamel compositions having a more decorative appearance were produced by including small pieces of light reflecting, decorative material known as glitters within the composition.

Other attempts to enhance the decorative appearance of nail enamel compositions has been the use of bismuth oxychloride pigments to produce a frosted effect. These compositions were based upon incorporation of bismuth oxychloride pigments with nitrocellulose or other polymers as the film forming component.

Although bismuth oxychloride provides a unique and decorative look to the nail enamel composition, the resulting films have been known to lack substantial gloss which detracts from their aesthetic value. There is theretofore the desire for nail enamel compositions which include bismuth oxychloride which, when applied to natural or synthetic human nails, will produce a film having an enhanced glossy appearance.

SUMMARY OF THE INVENTION

The present invention discloses a nail enamel composition having a glossy appearance, and more specifically, a frosted appearance having improved gloss characteristics. The nail enamel composition includes bismuth oxychloride pigments which are commercially available in a paste or powder form from a number of known suppliers, e.g., Rona EM Industries, Inc. of Hawthorne, N.J. sold under the mark Nailsyn which is a toluene free dispersion for use in nail enamel compositions. In accordance with the preferred embodiment, bismuth oxychloride pigments are obtained from the Mearl Corporation of New York under the name BIJU Utra UNT. BIJU Utra UNT is a pearly paste containing bismuth oxychloride crystals in a nitrocellulose vehicle with ester solvents. The bismuth oxychloride is present in the amount of about 58–62% by weight.

In accordance with the present invention, it has been discovered that nail enamel compositions containing bismuth oxychloride pigments can be formulated to have an improved glossy appearance. To this end, it has been discovered that by incorporating one or more film forming components into the nail enamel composition having higher molecular weights, the resulting composition will produce a film having an enhanced appearance. The film forming component in accordance with the preferred embodiment is nitrocellulose having a molecular weight greater than 56,000.

In accordance with one embodiment of the present invention there is described a nail enamel composition for forming a film over natural or synthetic human nails, the composition comprising nitrocellulose having a molecular weight greater than 56,000, a solvent and bismuth oxychloride.

In accordance with another embodiment of the present invention there is described a method of forming a film containing bismuth oxychloride over natural or synthetic human nails, the method comprising coating a natural or synthetic human nail with a nail enamel composition comprising nitrocellulose having a molecular weight greater than 56,000, a solvent and bismuth oxychloride.

DETAILED DESCRIPTION OF THE PREFERRED EMBODIMENTS

In describing the preferred embodiments of the present invention, specific terminology will be resorted to for the sake of clarity. However, the invention is not intended to be limited to the specific terms so selected, and is to be understood that each specific term includes all technical equivalence which operate in a similar manner to accomplish a similar purpose.

Nail enamel compositions of the present invention for coating natural or synthetic human nails broadly include the ingredients of one or more film forming components, one or more solvents and bismuth oxychloride pigments. The resulting composition will provide a nail enamel which forms a film upon drying having improved gloss and frosted appearance. In addition to the above components, the nail enamel compositions according to the present invention may further include one or more additional ingredients, for example, a thixotropic compound, a suspending agent, plasticizers, secondary pigments or colorants, one or more film forming resins, UV light absorbers, stabilizers, fragrances, moisturizers, leveling agents, drying agents and the like. In addition, if desired, the nail enamel compositions of the present invention may also include other pigments or organic coloring polymers to alter the film appearance as desired.

The nail enamel compositions of the present invention contain one or more primary film forming components such as polymers and the like. For example, suitable film forming compounds include cellulose acetate, cellulose acetate butyrate, ethyl cellulose, vinyl polymers, nitrocellulose, methacrylate and acrylate type polymers and co-polymers, and mixtures thereof. The preferred primary film forming compound for use in the present invention is nitrocellulose which provides an unusual combination of properties of toughness, durability, solubility and solvent release. Nitrocellulose is typically supplied in 70% concentrations, wet with 30% ethyl or isopropyl alcohol. As used in the present application, the percentage of nitrocellulose given in a composition will be on a dry basis.

It has been discovered that film forming compounds having higher molecular weights will produce films having improved gloss appearance when incorporating bismuth oxychloride. In this regard, it was determined that as the molecular weight of the film forming compound increased, the gloss appearance of the resulting nail enamel film improved as measured by its gloss property as to be described hereinafter. By way of example, nitrocellulose as the film forming compound having an average molecular weight greater than 56,000 show improvements in gloss appearance. To this end, nitrocellulose as a film forming compound is available from a variety of sources, for example, Hercules, Inc. in various molecular weights. These grades of nitrocellulose include nitrocellulose RS½ sec. having a molecular weight of 56,000, nitrocellulose RS5–6 sec. having a molecular weight of 112,000, nitrocellulose RS15 sec. having a molecular weight of 130,000, nitrocellulose RS60–80 sec. having a molecular weight of 175,000, nitrocellulose RS150 sec. having a molecular weight of 190,000, as well as other grades having both lower and higher molecular weights.

Although nitrocellulose having still higher molecular weights can also be used in the compositions of the present invention, they are less desirable due to their increased viscosity. It is contemplated that various grades of nitrocellulose can be used in combination as the film forming compounds of the present invention. For example, mixtures of low and high molecular weight nitrocellulose can be incorporated into the nail enamel compositions of the present invention. In particular, to improve the wear characteristics of the resulting film, the solid content of the nail enamel composition can be increased by using a mixture of lower grade nitrocellulose, e.g., RS¼ sec., and higher grade nitrocellulose, e.g., RS60–80 sec., the combination having an average molecular weight greater than 56,000.

Other film forming compounds include cellulose acetate butyrate Product No. 381-20 having a molecular weight of about 83,000 which is available from Eastman. It is contemplated that other film forming compounds can be used having molecular weights sufficiently high to provide a nail enamel composition having enhanced appearance. Nail enamel compositions of the present invention may include the above film forming compounds, their equivalence and combinations thereof in an amount ranging from about 2 to about 15% by weight, and more preferably in the range of about 4 to about 8% by weight of the composition.

In addition to the aforementioned film forming compounds, the nail enamel compositions can also include one or more modifying resins. Exemplary film resins which may be used in the present invention in combination with the film forming compounds include, for example, drying and non-drying alkyd resins, polyvinyl resins for example polyvinyl acetate, polyester resins, epoxy resins, acrylic polymers and copolymers, maleic modified glycerol esters of rosin, and toluene sulfonamide/epoxy resins, e.g., tosylamide epoxy resin. It is also within the scope of the present invention to include aldehyde condensation products such as arylsulfonamide formaldehyde resins, specifically toluene sulfonamide formaldehyde resin which is a condensation product of formaldehyde and toluene sulfonamide.

In addition to the film forming compounds, the nail enamel compositions according to the present invention may include at least one plasticizer to soften and plasticize particularly the film forming compounds. The plasticizer may be in either liquid or solid form, as well as combinations thereof. The compositions may include one or more of the known plasticizers which are suitable for use in nail enamel compositions. Examples of such known plasticizers include tricresyl phosphate, dibutyl tartrate, benzyl benzoate, tributyl phosphate, butyl acetyl ricinoleate, butyl glycolate, butyl stearate, sucrose acetate isobutyrate, triphenyl phosphate, triethyl citrate, camphor, castor oil, esters of citric, stearate, phalic, oleic, phosphate, butyric and benzoic acid, glyceryl triacetate and glyceryl triproprionate, 2,2,4-trimethyl-1,3-pentandiiol diisobutyrate and mixtures thereof. The nail enamel compositions of the present invention also contemplate the use of phthalate type plasticizers either alone or in combination with the aforementioned plasticizers, for example, diamylphthalate, dibutyl phthalate, diethyl phthalate, dioctyl phthalate, dibutoxy ethylphthalate and mixtures thereof. One preferred combination of plasticizers includes a mixture of dibutyl phthalate and sucrose acetate isobutyrate. Plasticizers included in the compositions of the present invention are in amounts sufficient to provide acceptable flexibility to the nail enamel film on the human or synthetic nail surface.

The nail enamel compositions of the present invention also include one or more organic solvents such as those generally used in conventional nail enamel compositions. Examples of these solvents include ethyl acetate, methyl acetate, ethanol, isopropanol, propyl acetate, n-butanol, xylene, DI acetone alcohol, aromatic (containing phenyl groups), amyl acetate, ethers, ketones, alkanes for example, pentane, cyclopentane, hexane, toluene, heptane, cyclohexane, cyclic ethers for example, tetrahydrofuran and 1,4-dioxane, cellosolve, butyl cellosolve acetate, cellosolve acetate, methyl cellosolve acetate, butyl cellosolve, ethyl cellosolve, phenylated solvents for example, xylene, esters of acetic acid for example, methyl acetate, ethyl acetate, n-butyl acetate, chlorinated hydrocarbons for example, methylene chloride, chloroform and methylchloroform. The aforementioned solvents can be used alone or in mixtures thereof. In general, the amount of solvent used in the compositions of the present invention range from about 80 to about 96% by weight, and preferably about 85 to about 90% by weight of the composition.

The nail enamel compositions of the present invention may include bismuth oxychloride pigments in an amount ranging from about 0.75 to about 6% by weight on a dry basis, and preferably in the range of about 2.4% by weight of the composition.

Additionally, secondary pigments and/or organic colorants can be added to the compositions to provide cosmetically acceptable shades and to pacify the films. Pigments and/or organic colorants for use in the present invention may include any of those pigments or organic colorants which are generally known for use in nail enamel compositions. For example, pigments can include cosmetic grade or purified titanium dioxide, yellow and red iron oxides, aluminum platelets, iron blue, iron black, mica particles, ultramarine blue, D&C Red #7, chromide oxide greens, carbon black, lampblack and the like. Other pigments which may be used in compositions according to the present invention may include the Lake pigments, for example, D&C Red #6 barium Lake, D&C Red #7 calcium Lake and the like.

In addition to the above named pigments, there may also be included titanated micas, polyethylene teraphthalates and pearl essence which is a suspension of crystalline guanine in nitrocellulose and solvents, as well as other additives which will affect the appearance of the pigment. The amount of pigment in the compositions of the present invention will vary as a function of the type of pigment and other components included in the composition.

It is useful to include a suspending agent for enhancing the suspension of the bismuth oxychloride or other pigments in the other components of the nail enamel composition. A number of suspending agents, either alone or in combination, which are generally used in conventional nail enamel compositions may be used to produce compositions according to the present invention. For example, suspending agents include colloidal clays, montmorillonite clays, especially stearalkonium hectorite, stearalkonium bentonite, fumed silica, and mixtures thereof. One preferred combination of suspending agents include bentonite and a modified lower molecular weight polymeric urea available from BYK-Chemie USA, Wallingford, Conn. sold under the name BYK-410. The suspending agent is present in the compositions of the present invention in amounts sufficient to produce a gel, preferably a colloidal gel. It is also contemplated that the polymeric urea can be used alone as a suspending agent.

In addition to the above described components, the nail enamel compositions of the present invention may also include additional additives including stabilizers, thixotropic agents, UV light absorbers such as ectocrylene and benzophenone-1, fragrances, moisturizers and medicants, depending on the intended result. These components are well known in the art and may be included in amounts well within the teachings of the prior art.

The incorporation of higher molecular weight components into the nail enamel composition of the present invention has the tendency to increase the composition viscosity. To maintain the composition in a flowable state to allow smooth and even application to one's nails, the percentage of solids in the composition can be reduced if desired. By way of example, the solid content of the nail enamel compositions of the present invention ranges from about 4 to about 20% by weight, and preferably from about 10 to about 15% by weight. These examples are by way of illustration and are not intended to be limiting of the present invention either as to the inclusion of a greater or lesser number of components, the substitution of additional components or variations in the percentages of the range of components.

The nail enamel compositions in accordance with the present invention can be manufactured by thoroughly and intimately mixing together all the components in the amounts described in accordance with the present invention. Examples of satisfactory equipment and how to use then are readily apparent to one of ordinary skill in the nail enamel art. The nail enamel compositions of the present invention are generally applied directly over one's nail. However, these compositions may be applied over base coats which are clear or are pigmented.

In order to evaluate the gloss characteristics of various nail enamel compositions prepared which include bismuth oxychloride pigments, an instrument known as a goniophotometer was used. A goniophotometer is an instrument for measuring the angular distribution of reflected or transmitted light. In this regard, the appearance of nail enamel compositions which include bismuth oxychloride pigments can be described by its gloss characteristics. The term "gloss" is defined in ASTM standard E284(3) entitled Terminology of Appearance as angular selectivity of reflectance, involving surface-reflected light, responsible for the degree to which reflected highlights or images of objects may be seen as superimposed on a surface. Angular selectivity falls into various types such as specular gloss, sheen and haze. "Specular gloss" is defined in the aforementioned ASTM standard as the ratio of flux reflected in specular direction to incident flux for a specified angle of incidence and source and receptor angle apertures. "Sheen" is defined in the aforementioned ASTM standard as the specular gloss at a large angle of incidence for an otherwise matte specimen. Haze in coating films is often designated "reflection haze" because in plastics there is encountered a near-forward scattering in transmission that is designated transmission haze. The aforementioned ASTM standard defines "haze" in reflection as percent of reflected light scattered by a specimen having a glossy surface so that its direction deviates more than a specified angle from the direction of specular reflection. One instrument suitable for measuring the properties of gloss of a film using a 60° angle is available from BYK Gardner USA of Columbia, Md., Catalog No. GL-4520.

Samples for evaluation were based upon a dried 6 mil wet film drawn on a substrate obtained from The Linetta Company of Mahwah, N.J. The evaluated compositions were based upon incorporation of bismuth oxychloride pigments with nitrocellulose as the primary film forming component, and cellulose acetate butyrate as a secondary film forming component. The compositions evidenced that the gloss characteristics of the film, as measured by gloss values, is improved as the molecular weight of the resulting film increases, e.g., increasing in gloss from 81 gloss units (control composition) to 118 gloss units using the composition of the present invention including mixtures of nitrocellulose and cellulose acetate butyrate with 2.4% bismuth oxychloride on a dry basis. By way of example, increased molecular weight of the overall film is a function of not only the primary film forming compound, but also any modifying resin and the incorporation of plasticizers and the like. In the case of nitrocellulose as the primary film-forming compound, improvements in gloss appearance were obtained as the average molecular weight of the nitrocellulose increased above 56,000.

In accordance with one embodiment of the present invention, a formulation for a nail polish including bismuth oxychloride is as follows:

| INGREDIENTS | WEIGHT PERCENTAGE |
| --- | --- |
| ETHYL ACETATE | 38.46 |
| BUTYL ACETATE | 24.10 |
| ETHYL ALCOHOL | 9.00 |
| NITROCELLULOSE | 7.30 |
| ISOPROPYL ALCOHOL | 6.30 |
| AMYL ACETATE | 5.00 |
| BISMUTH OXYCHLORIDE | 2.40 (dry) |
| SUCROSE ACETATE ISOBUTYRATE | 2.30 |
| DIBUTYL PHTHALATE | 1.60 |
| CAMPHOR | 1.35 |
| STEARALKONIUM HECTORITE | 1.10 |
| DIACETONE ALCOHOL | 0.70 |
| PHOSPORIC ACID | 0.03 |
| CITRIC ACID | 0.01 |
| DIMETHICONE | 0.01 |
| FD&C YELLOW #5 ALUMINUM LAKE | 0.08 |
| FERRIC AMMONIUM FERROCYANIDE | 0.05 |
| BLACK IRON OXIDE | 0.21 |

In accordance with the present invention, nail enamel compositions which include bismuth oxychloride pigments can be produced having improved gloss appearance. The films can achieve these results by selecting the film forming polymer and resulting composition to have a sufficiently high molecular weight. Once the particular type of film forming compound is selected, e.g., nitrocellulose, compounds of varying molecular weight can be evaluated for the resulting gloss appearance. These results will be influenced by the molecular weight of the other components which are added to the nail enamel composition, for example, plasticizers, resins and the like. From the foregoing, one can produce a nail enamel composition in accordance with the present invention having an improved gloss appearance based upon selected components, e.g., film formers, plasticizers, etc.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A nail enamel composition for forming a film over natural or synthetic human nails, said composition comprising nitrocellulose having a molecular weight greater than 56,000, a solvent and bismuth oxychloride, wherein said film has a gloss value greater than a gloss value of the same film containing nitrocellulose having a molecular weight less than 56,000.

2. The composition of claim 1, wherein said nitrocellulose has a molecular weight greater than 112,000.

3. The composition of claim 1, wherein said bismuth oxychloride is in the form of a paste.

4. The composition of claim 3, wherein said paste includes butyl acetate, isopropyl alcohol, nitrocellulose and stearalkonium hectorite.

5. The composition of claim 1, wherein said solvent is selected from the group consisting of toluene, normal propyl acetate, isopropyl acetate, isopropyl alcohol, ethyl acetate, glycol ether pm, normal butyl acetate, methyl propyl acetate and mixtures thereof.

6. The composition of claim 1, further comprising a plasticizer and a suspending agent.

7. The composition of claim 6, wherein said plasticizer comprises a mixture of dibutyl phthalate and sucrose acetate isobutyrate.

8. The composition of claim 6, wherein said suspending agent comprises a mixture of bentonite and polymeric urea.

9. The composition of claim 1, wherein said bismuth oxychloride is present in the range of from 0.75 to 10% by weight of said composition.

10. The composition of claim 1, wherein said bismuth oxychloride is present in the amount of 2.4% by weight of said composition.

11. The composition of claim 1, wherein the solid content of said composition is in the range of from about 10 to about 15% by weight of said composition.

12. The composition of claim 1, wherein said nitrocellulose is present in at least two grades, one having a molecular weight greater than 56,000 and one having a molecular weight less than 56,000, the average molecular weight being greater than 56,000.

13. The composition of claim 1, wherein said bismuth oxychloride is in the form of a powder.

14. A method of forming a film containing bismuth oxychloride over natural or synthetic human nails, said method comprising coating a natural or synthetic human nail with a nail enamel composition comprising nitrocellulose having a molecular weight greater than 56,000, a solvent and bismuth oxychloride, wherein said film has a gloss value greater than a gloss value of the same film containing nitrocellulose having a molecular weight less than 56,000.

15. The method of claim 14, wherein said nitrocellulose has a molecular weight greater than 112,000.

16. The method of claim 14, wherein said bismuth oxychloride is in the form of a paste.

17. The method of claim 16, wherein said paste includes butyl acetate, isopropyl alcohol, nitrocellulose and stearalkonium hectorite.

18. The method of claim 14, wherein said solvent is selected from the group consisting of toluene, normal propyl acetate, isopropyl acetate, isopropyl alcohol, ethyl acetate, glycol ether pm, normal butyl acetate, methyl propyl acetate and mixtures thereof.

19. The method of claim 14, further comprising a plasticizer and a suspending agent.

20. The method of claim 19, wherein said plasticizer comprises a mixture of dibutyl phthalate and sucrose acetate isobutyrate.

21. The method of claim 19, wherein said suspending agent comprises a mixture of bentonite and polymeric urea.

22. The method of claim 14, wherein said bismuth oxychloride is present in the range of from 0.75 to 10% by weight of said composition.

23. The method of claim 14, wherein said bismuth oxychloride is present in the amount of 2.4% by weight of said composition.

24. The method of claim 14, wherein said nitrocellulose is present in at least two grades, one having a molecular weight greater than 56,000 and one having a molecular weight less than 56,000, the average molecular weight being greater than 56,000.

25. The method of claim 14, wherein said bismuth oxychloride is in the form of a powder.

* * * * *